(12) United States Patent
Bergendahl et al.

(10) Patent No.: US 7,892,830 B2
(45) Date of Patent: Feb. 22, 2011

(54) CLONAL CULTURE OF HUMAN PLURIPOTENT STEM CELLS

(75) Inventors: Veit Bergendahl, Madison, WI (US); James A. Thomson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/016,066

(22) Filed: Jan. 17, 2008

(65) Prior Publication Data

US 2008/0171385 A1 Jul. 17, 2008

Related U.S. Application Data

(60) Provisional application No. 60/880,747, filed on Jan. 17, 2007.

(51) Int. Cl.
*C12N 5/00* (2006.01)
*C12N 5/02* (2006.01)
*C12N 5/071* (2010.01)

(52) U.S. Cl. .................. 435/384; 435/325; 435/366; 435/383; 435/402; 435/404; 435/405

(58) Field of Classification Search ............... 435/384, 435/325, 366, 383, 402, 404, 405
See application file for complete search history.

(56) References Cited

U.S. PATENT DOCUMENTS

| 4,525,589 | A | 6/1985 | Kaisha et al. |
|---|---|---|---|
| 6,153,608 | A | 11/2000 | Hidaka et al. |
| 6,218,410 | B1 | 4/2001 | Uehata et al. |
| 6,451,825 | B1 | 9/2002 | Uehata et al. |
| 6,906,061 | B2 | 6/2005 | Uehata et al. |
| 7,439,064 | B2 | 10/2008 | Thomson et al. |
| 7,442,548 | B2 | 10/2008 | Thomson et al. |
| 7,449,334 | B2 | 11/2008 | Thomson et al. |
| 2006/0172414 | A1* | 8/2006 | Weissman et al. ........... 435/354 |
| 2008/0021026 | A1 | 1/2008 | Kahraman et al. |
| 2008/0021217 | A1 | 1/2008 | Borchardt et al. |

FOREIGN PATENT DOCUMENTS

| JP | 98/06433 | 2/1998 |
|---|---|---|
| WO | 03/080649 A | 10/2003 |
| WO | 2004/078917 | 9/2004 |
| WO | 2006020919 A3 | 2/2006 |
| WO | 2008/035110 | 3/2008 |
| WO | 200803511 A1 | 3/2008 |

OTHER PUBLICATIONS

Lim et al. Proteomics, 2:1187-1203, 2002.*
Prowse et al. Proteomics, 5:978-989, 2005.*
Thomson. PNAS, 92: 7844-7848, Aug. 1995.*
Oh et al. Clin. And Exp. Pharmacology and Physiology, 33:489-495, 2006.*
Ludwig et al. Nat. Biotech., 24(2): 185-187, 2006.*
Xu et al. Nature Biotech.,19: 971-974, 2001.*
Amit et al. Dev. Biol., 227: 271-278, 2000.*
Amit et al. Biol. Of Reprod., 70:837-845, 2004.*
Mallon et al. The Int. Journal of Biochem. & Cell Bio, 38: 1063-1075, 2006.*
Ludwig T, et al., "Feeder-independent culture of human embryonic stem cells," Nat. Methods 3:637-646 (2006).
Watanabe K, et al., "A Rock inhibitor permits survival of dissociated human embryonic stem cells," Nat. Biotechnol. 25:681-686 (2007).
Beattie G, et al., "Activin A maintains pluripotency of human embryonic stem cells in the absence of feeder layers," Stem Cells 23:489-495 (2005).
Chen S, et al., "Self-renewal of embryonic stem cells by a small molecule," Proc. Natl. Acad. Sci. USA 103:17266-17271 (2006).
Ding S & Schultz P, "Small molecules and future regenerative medicine," Curr. Top. Med. Chem. 5:383-395 (2005).
Norman T, "Human embryonic stem cells: a resource for in vitro neuroscience research?," Neuropsychopharmacology 31:2571-2572 (2006).
Park H, et al., "mGluR5 is involved in dendrite differentiation and excitatory synaptic transmission in NTERA2 human embryonic carcinoma cell-derived neurons," Neuropharmacology 52:1403-1414 (2007).
Du, Xinyu et al., "Protein Kinase C Activators Work in Synergy with Specific Growth Factors to Initiate Tyrosine Hydroxylase Expression in Striatal Neurons in Culture," Journal of Neurochemistry, vol. 68, No. 2: 564-569 (1997).
Ikenoya, Mami et al., "Inhibition of Rho-kinase-induced myristoylated alanine-rich C kinase substrate (MARCKS) phosphorylation in human neuronal cells by H-1152, a novel and specific Rho-kinase inhibitor," Journal of Neurochemistry 81: 9-16 (2002).
Posypanova, Galina A., "Effect of Protein Kinase Modulators on the Induction of Morphological Differentiation of Pheochromocytoma PC12 Cells by Nerve and Fibroblast Growth Factors," Biotechnology and Applied Biochemistry 12: 20-27 (1990).
Sasaki, Yasuhar et al., The novel and specific Rho-kinase inhibitor (S)-(+)-2-methyl-1-[4-methyl-5-isoquinoline) sulfonyl]-homopiperazine as a probing molecule for Rho-kinase-involved pathway; Pharmacology & Therapeutics 93: 225-232 (2002).

* cited by examiner

*Primary Examiner*—Thaian N Ton
(74) *Attorney, Agent, or Firm*—Quarles & Brady LLP

(57) ABSTRACT

While culture medium and systems have been described that permit the culture and proliferation of human embryonic stem cells in feeder free and animal product free conditions, these conditions will not readily support cloning of an embryonic stem cell culture meaning, at least here, the initiation of a sub-culture using one or a very few originating cells. It has been found here that a class of small molecules that are inhibitors of kinase enzymes will increase the efficiency of cloning of stem cell cultures sufficiently to make such cloning practical in the defined medium and in other media as well.

8 Claims, No Drawings

CLONAL CULTURE OF HUMAN PLURIPOTENT STEM CELLS

CROSS-REFERENCE TO RELATED APPLICATIONS

This application claims the benefit of U.S. Provisional Patent Application No. 60/880,747, filed Jan. 17, 2007, incorporated herein by reference as if set forth in its entirety.

STATEMENT REGARDING FEDERALLY SPONSORED RESEARCH OR DEVELOPMENT

Not applicable.

BACKGROUND

Embryonic stem (ES) cells are pluripotent cells capable of both proliferation in cell culture and differentiation towards a variety of lineage-restricted cell populations that exhibit multipotent properties (Odorico et al., Stem Cells 19:193-204 (2001)). Because of these characteristics, ES cells, including human ES cells, can become very specific cell types that perform a variety of functions.

Generally, human ES cells are highly homogeneous, have a capacity for self-renewal and have an ability to differentiate into any functional cell in the body. Self-renewal can, under appropriate conditions, lead to a long-term proliferating capability with a potential for unlimited expansion in cell culture. In addition, if human ES cells differentiate in an undirected fashion, a heterogeneous population of cells is obtained that express markers for a plurality of different tissue types (WO 01/51616; and Shamblott et al., Proc. Natl. Acad. Sci. USA 98:113 (2001)). These features make human ES cells a unique, homogeneous, starting population for the production of cells having therapeutic utility.

Human ES cells can be used to make a variety of differentiated cells types for scientific and commercial research use. At present, differentiated human cells of many types are not readily available and cannot be expanded in significant numbers in in vitro culture. Human ES cells, however, can expand indefinitely in culture and can differentiate into many, if not all, the differentiated cell types of the human body. As such, culture techniques are being developed to induce human ES cells to differentiate into any number of specific cell types of the human body. The availability of human ES cells has opened the possibility that many differentiated human cells will become available in significant numbers for scientific and commercial research.

One difficulty in working with human ES cells is the development of conditions for the standardized culture of human ES cells without the use of animal products or products such as serum, which tend to vary from batch to batch. As such, the art desires culture conditions of human ES cell culture to be as defined as possible.

To work toward that desire, a set of culture conditions was recently described that permitted the long-term culture of undifferentiated human ES cells in defined conditions. Ludwig et al., Nat. Methods 3:637-646 (2006), incorporated herein by reference as if set forth in its entirety. Ludwig et al. described a medium, referred to herein as TeSR™ medium, for cultivation of human ES cells in which each constituent of the medium was fully disclosed and characterized. TeSR™ is therefore a fully defined and sufficient medium for human ES cell culture. TeSR™ has proven effective for use in the derivation of new human ES cell lines as well, which is an even more challenging constraint than the culture of undifferentiated human ES cells.

Human ES cells preferentially remain undifferentiated when grown in environments in which the cells are in direct contact with other cells or with physical structures in their environment. In other cellular environments, human ES cells begin to differentiate and become incapable of indefinite proliferation.

This is significant in the process of cloning an ES cell culture. As used herein, "cloning" means a process of initiating an ES cell culture from a starting culture, ideally, from a single ES cell or at least from very few ES cells. Culture conditions that permit clonal culture of undifferentiated ES cells may be the most demanding conditions of all of those required in normal ES cell culture and proliferation.

BRIEF SUMMARY

In a first aspect, the present invention is summarized as a method for cloning a pluripotent stem cell culture that includes the steps of providing a culture of pluripotent stem cells in culture in a defined culture medium in a culture vessel; selecting a single cell from the stem cells in the culture; and initiating a new culture of the stem cells in the culture medium in a culture vessel with the single cell, the culture medium including an agent selected to increase the cloning efficiency of the stem cell culture, the agent being a small molecule that increases cloning efficiency of the stem cell culture. By "defined culture medium" or "defined medium," we mean that the medium has known quantities of all ingredients. Typically, serum that is normally added to culture medium for cell culture is replaced by known quantities of serum components, such as, e.g., albumin, insulin, transferrin and possibly specific growth factors (i.e., basis fibroblast growth factor, transforming growth factor or platelet-derived growth factor).

In a second aspect, the present invention is summarized as a pluripotent stem cell culture that includes a culture vessel; a defined culture medium contained in the vessel; stem cells growing in the culture medium; and an agent in the culture medium selected to increase cloning efficiency of the stem cell culture.

In some embodiments of the either aspect, the agent is a kinase inhibitor. In other embodiments of the either aspect, the agent is a protein kinase A inhibitor, a protein kinase C inhibitor, a protein kinase G inhibitor or a Rho-associated kinase inhibitor. In still other embodiments of the either aspect, the agent is selected from H-7, iso H-7, H-8, H-9, H-89, HA-100, HA-1004, HA-1077, H-1152 or Y-27632.

It is an object of the present invention to improve techniques for the culture of pluripotent stem cells, including increasing the cloning efficiency of culture conditions. By pluripotent stem cells, we mean ES cells or induced pluripotent stem (iPS) cells. iPS cells are reprogrammed differentiated somatic cells that may vary with respect to their differentiated somatic cell of origin, that may vary with respect a specific set of potency-determining factors and that may vary with respect to culture conditions used to isolate them, but nonetheless are substantially genetically identical to their respective differentiated somatic cell of origin and display characteristics similar to higher potency cells, such as ES cells It is an advantage of the present invention that cloning efficiency of stem cell culture conditions can be improved by the addition of one of a group of small molecules to the stem cell culture, the small molecules being economical and effective.

These and other features, aspects and advantages of the present invention will become better understood from the description that follows. The description of preferred embodiments is not intended to limit the invention to cover all modifications, equivalents and alternatives. Reference should therefore be made to the claims herein for interpreting the scope of the invention.

BRIEF DESCRIPTION OF THE SEVERAL VIEWS OF THE DRAWINGS

Not applicable.

DETAILED DESCRIPTION OF EXEMPLARY EMBODIMENTS

As described above, a difficulty in growing pluripotent cells, like ES cells, in culture is their low cloning efficiency. As used herein, "cloning efficiency" means a number of cells individualized by trypsin that form new ES cell colonies divided by the number of individual cells plated in a well of a culture dish. In our prior experience with growing human ES cells in defined and animal-free conditions on a matrix (e.g., Matrigel®), cloning efficiency was very low (i.e., less than 0.1%). This contrasts with prior experience using culture systems based on medium conditioned by exposure to fibroblasts, where the cloning efficiency, while still low (i.e., less than 2%), was high enough to initiate clonal ES cell colonies. As disclosed herein, the addition of a small molecule to the culture medium in which human ES cells are grown permits the ES cell cultures to be clonally cultivated in a manner that is extremely difficult without the addition of the small molecule. Several small molecules are exemplified herein for this purpose.

As a point of clarification, there is a difference between "passaging" human ES cells and initiating clonal colonies. In typical practice in ES cell cultivation, when a culture container is full, the colony is split into aggregates, which are then placed into new culture containers. These aggregates typically contain 100 to 1,000 cells, which readily initiate growth in culture. In contrast, initiating clonal colonies requires growing human ES cell colonies from single individual ES cells.

The small molecules identified herein that act as agents to increase the cloning efficiency of ES cells were identified by a screen of small molecules for this purpose. The mechanism by which these small molecules enhanced cloning efficiency of the culture of human ES cells is unknown. Presumably, the small molecules interact with a signaling kinase to alter a signaling pathway in the cells, but the identity of the interaction and the pathway are not known at present. Regardless of the mechanism of action, the small molecules effectively increased the cloning efficiency of ES cell culture, which was evident even in differing culture conditions.

The screen was conducted using a fluorescent, high-throughput assay to screen small molecules for their ability to enhance cloning efficiency. A soluble, non-fluorescent substrate (6,8-difluoro-4-methylumbelliferyl phosphate, DiFMUP) was converted to a fluorescent product by an enzyme specific for undifferentiated, human ES cells called alkaline phosphatase (ALP).

In wells that had colonies larger than 2,000 cells, and which formed 12 days after seeding 500 individualized human ES cells in a 96-well plate, increased fluorescence from DiFMUP hydrolyzed by ALP indicated any well that contained a compound that enabled colony formation. Cells that proliferated lost ALP activity upon differentiation and did not rise to increased fluorescence,. Thus, this assay tested both for clonal propagation and for maintenance of undifferentiated status.

Using the methods described herein, a set of small molecules for increasing the efficiency of ES cell cloning was identified. One preferred small molecule is (S)-(+)-2-methyl-1-[(4-methyl-5-isoquinolinyl)sulfonyl]homopiperazine dihydrochloride (informal name: H-1152). Another preferred small molecule is 1-(5-isoquinolinesulfonyl)piperazine hydrochloride (informal name: HA-100). Although both appear equally effective in facilitating clonal growth, H-1152 can be used at ten times lower working concentrations than HA-100. Other related small molecules that were also effective included the following: 1-(5-isoquinolinesulfonyl)-2-methylpiperazine (informal name: H-7), 1-(5-isoquinolinesulfonyl)-3-methylpiperazine (informal name: iso H-7), N-2-(methylamino)ethyl-5-isoquinoline-sulfonamide dihydrochloride (informal name: H-8), N-(2-aminoethyl)-5-isoquinolinesulphonamide dihydrochloride (informal name: H-9), N-[2-p-bromo-cinnamylamino)ethyl]-5-isoquinolinesulfonamide dihydrochloride (informal name: H-89), N-(2-guanidinoethyl)-5-isoquinolinesulfonamide hydrochloride (informal name: HA-1004), 1-(5-isoquinolinesulfonyl)homopiperazine dihydrochloride (informal name: HA-1077), (S)-(+)-2-Methyl-4-glycyl-1-(4-methylisoquinolinyl-5-sulfonyl)homopiperazine dihydrochloride (informal name: glycyl H-1152) and (+)-(R)-trans-4-(1-aminoethyl)-N-(4-pyridyl)cyclohexanecarboxamide dihydrochloride (informal name: Y-27632). Each small molecule supported a cloning efficiency >1% in a defined medium, such as TeSR™1 medium, on Matrigel®-coated culture dishes. The full constituents and methods of use of the TeSR™1 medium are described in Ludwig et al. Ludwig et al., supra.

The effect conditioned by these small molecules was not limited to the use of TeSR™1 medium. These small molecules also increased cloning efficiency of ES cell cultures grown on conditioned medium, which is medium that has been exposed to fibroblasts. It is thus believed that these small molecules increase the cloning efficiency of any ES cell culture medium in which ES cells can effectively be grown.

A class of small molecules effective for increasing the cloning efficiency of a ES cell culture medium are inhibitors of kinase enzymes, including protein kinase A (PKA), protein kinase C (PKC), protein kinase G (PKG) and Rho-associated kinase (ROCK).

Of particular interest herein are ROCKs. ROCKs are serine/threonine kinases that serve as a target proteins for Rho (of which three isoforms exist—RhoA, RhoB and RhoC). Theses kinases were initially characterized as mediators of the formation of RhoA-induced stress fibers and focal adhesions. The two ROCK isoforms—ROCK1 (p160ROCK, also called ROKβ) and ROCK2 (ROKα)—are comprised of a N-terminal kinase domain, followed by a coiled-coil domain containing a Rho-binding domain and a pleckstrin-homology domain (PH). Both ROCKs are cytoskeletal regulators, mediating RhoA effects on stress fiber formation, smooth muscle contraction, cell adhesion, membrane ruffling and cell motility. ROCKs exert their biogical activity by targeting downstream molecules, such as myosin light chain (MLC), MLC phosphatase (MLCP) and the phosphatase and tensin homolog (PTEN).

An exemplary ROCK inhibitor is Y-27632, which selectively targets ROCK1 (but also inhibits ROCK2), as well as inhibits TNF-α and IL-1 β. It is cell permeable and inhibits ROCK1/ROCK2 ($IC_{50}$=800 nM) by competing with ATP. Ishizaki T, et al., Mol. Pharmacol. 57:976-983 (2000), incorporated herein by reference as if set forth in its entirety. Other ROCK inhibitors include, e.g., H-1152, Y-30141, Wf-536, HA-1077, hydroxyl-HA-1077, GSK269962A and SB-772077-B. Doe C, et al., J. Pharmacol. Exp. Ther. 32:89-

98 (2007); Ishizaki et al., supra; Nakajima M, et al., Cancer Chemother. Pharmacol. 52:319-324 (2003); and Sasaki Y, et al., Pharmacol. Ther. 93:225-232 (2002), each of which is incorporated herein by reference as if set forth in its entirety.

The small molecules identified herein have at least a pyridine as a common structural element. As such, other small molecules useful herein include, e.g., N-(4-Pyridyl)-N'-(2,4,6-trichlorophenyl)urea, 3-(4-Pyridyl)-1H-indole and (R)-(+)-trans-N-(4-Pyridyl)-4-(1-aminoethyl)-cyclohexanecarboxamide.

The data presented below and discussed above demonstrate that a class of small molecule increased the cloning efficiency of human ES cell culture medium in general. In general, the class of effective small molecules is summarized as:

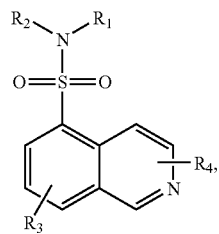

where $R_1$ and $R_2$ can connect through an aromatic group or $R_1$ is hydrogen or an alkyl, and $R_2$ is hydrogen or an alkyl, and $R_1$ is not the same as $R_2$ unless $R_1$ and $R_2$ are part of a cyclic aromatic, and where $R_3$ and $R_4$ are attached to any atom in the isoquinoline and are a hydrogen or an alkyl.

EXAMPLES

Example 1

Identification of Small Molecules that Increase ES Cell Cloning Efficiency

Methods and Materials.

The small molecules effective to enable cloning of ES cell colonies in the defined medium were identified in a small molecule screen for the desired activity of enabling cloning.

The screen used a small molecule library made up of characterized compounds with known bioactivity that was purchased from Sigma-Aldrich (St. Louis, Mo.). Members of the library were dissolved in DMSO to a concentration of 1 mM. All other chemicals used were purchased from Sigma, unless otherwise indicated in the text. H1 human ES cells (WiCell Research Institute; Madison, Wis.) were grown in the defined TeSR™1 medium, which was prepared as described in Ludwig et al., supra.

The assay was performed at the Keck-UWCCC Small Molecule Screening Facility (University of Wisconsin—Madison; Madison, Wis.) in 96-well microplates (Nunclon/Nunc; Roskilde, Denmark) using a Beckman Biomek® FX Laboratory Workstation and a Perkin Elmer VictorIII® Plate Reader. The microplates were coated with Matrigel® (#354230, growth factor reduced; BD Bioscience; San Jose, Calif.) at 0.3 mg/ml in DMEM/F12 (Invitrogen; Carlsbad, Calif.) for 1 hour at room temperature.

H1 human ES cells were grown in 6-well Nunclon® dishes to day 5, and then treated with 1 ml Trypsin/EDTA (Invitrogen) containing 1% chick serum for 5 minutes at 37° C. Trypsin was quenched with 20% FBS in DMEM/F12, and the cells were collected by centrifugation for 1.5 minutes at 200 RCF. After aspiration of the medium, cells were re-suspended in TeSR™1 medium to a density of 5,000 cells per ml. Of this cell suspension, 100 µL was dispensed into each well, and 1 µL of a 10 mM DMSO solution of inhibitor was added and mixed by pipetting, resulting in a final inhibitor concentration of 10 µM. The plates were incubated at 5% $CO_2$ at 37° C. for 2 days. Then, the medium was exchanged with TeSR™1 medium not having the cloning molecule. The plates were cultured for an additional 8 days, changing the medium every other day.

To detect colony formation, we used a fluorometric, ALP assay (EnzChek®; Invitrogen). In this assay, a soluble, non-fluorescent substrate (DiFMUP) is. converted to a fluorescent product by ALP. The plates were washed with 50 mM TrisHCl (pH 7.5) and treated with 100 µL of a 38 µM DiFMUP solution for 1 hour. In wells that had colonies, increased fluorescence indicated any well containing a compound that led to colony formation. Cells that proliferated, but also differentiated, did not give rise to increased fluorescence, as these cells lacked ALP activity. Plates were read by a multi-plate reader (excitation 355 nm, emission 455 nm, at 0.1 ms emission intervals).

Compounds that showed activity in the screen were tested in 6-well plates in 1% DMSO with varying concentrations. For these assays, 10,000 cells per well were plated on Matrigel®—coated plates and then treated every other day for a total of four days. with the small molecules as described above. To evaluate the effect of the tested small molecules on cloning efficiency, we manually counted colonies after 10 days.

We have also tested these small molecules for effects on human ES cell cloning on other medium. We tested the effect on conditioned medium (CM) substituting TeSR™1 medium with CM and otherwise identical treatment. The cloning efficiency of the medium increased with addition of HA-100. In addition, we performed a similar test with unconditioned medium to which 100 ng/µl of bFGF had been added. Again, the addition of HA-100 increased cloning efficiency compared to similar control cultures, which lacked HA-100.

Results.

The results of the small molecule screen were units of relative fluorescence. A typical performance of the fluorometric assay resulted in a mean value of 17,868, standard deviation of 5,104 and a standard error of 197. A typical hit (meaning that a colony grew) resulted in a reading of above 200,000. All potential hits were confirmed by visual inspection of the sample well. A clear colony of about 1 mm diameter was observed in wells with a true positive. We obtained 4 hits out of 4,500 individual samples. The hits were HA-100, lathosterol (a cholesterol precursor), obacunol (a limonoid) and quipazine dimaleate (a serotonin 2A agonist). Out of these four compounds, only HA-100 could be confirmed in the 6-well assay as active in increasing the cloning efficiency of cultured human ES cells.

We determined cloning efficiency (CE; the number of colony forming units (CFU) per number of plated single cells, trypsin/EDTA treated). HA-100 was the first molecule identified in the small molecule screen, following which other structurally similar small molecules were also tested for cloning efficiency. The following compounds showed similar activity within a certain concentration range, and the $IC_{50}$ values for three kinases (e.g., PKA, PKC and PKG) with the small molecules are listed below in Table 1:

HA-100 (Sigma), which has the following structure:

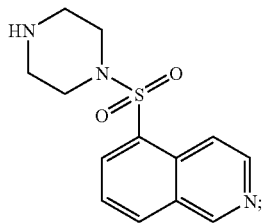

H-7 (Sigma), which has the following structure:

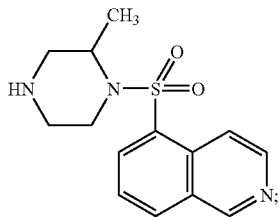

iso H-7 (Sigma), which has the following structure:

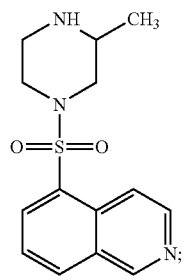

H-89 (Sigma), which has the following structure:

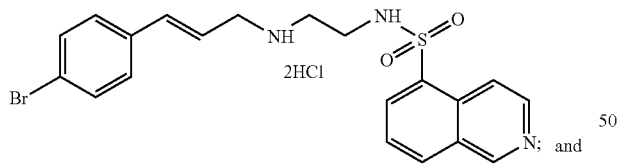

HA-1004 (Sigma), which has the following structure:

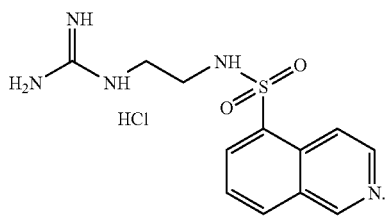

TABLE 1

| Molecule | HA-100 | H-7 | isoH-7 | H-89 | HA-1004 |
|---|---|---|---|---|---|
| PKA | 8 µM | 3 µM | >3 µM | 0.048 µM | 2.3 µM |
| PKC | 12 µM | 6 µM | >6 µM | 31.7 µM | 40.0 µM |
| PKG | 4 µM | 5.8 µM | >5.8 µM | 0.48 µM | 1.3 µM |
| CFU+ | 25-2 µM | 50-10 µM | 50-10 µM | 25-0.1 µM | >50.0 µM |
| max. CE (%) | 2 | <1 | <1 | 2.5 | <1 |

In addition, all small molecules were tested in conditioned medium (CM), which revealed up to a 30% cloning efficiency in CM with the small molecule as compared to CM alone.

We also tested the resulting colonies from HA-100 treatment for the presence of Oct4, an intracellular marker for pluripotent ES cells. The immunofluorescence showed clear evidence for the maintenance of Oct4 expression in treated cells in the cloned colonies, indicating undifferentiated status. This indicates that human ES cells can be individualized by trypsin and cultured in the presence of HA-100 without losing their pluripotency.

Subsequently, other related small molecules were also tested for their competence to increase cloning efficiency of human ES cells. HA-1077 (Upstate Biotechnologies; Lake Placid, N.Y.) increased cloning efficiency, which has the following structure:

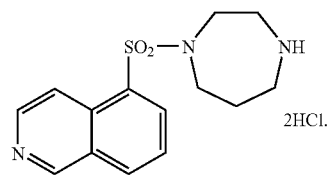

Two other related small molecules also showed similar effects. The first small molecule was H-8 (Biomol; Plymouth Meeting, Pa.), which has the following structure:

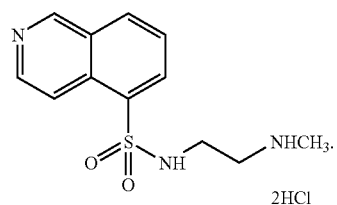

The second small molecule was H-9 (Biomol), which has the following structure:

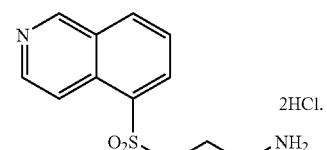

One small molecule, however, did not increase cloning efficiency of human ES cells. This small molecule was 1-[N, O-bis-(5-isoquinolinesulfonyl)-N-methyl-L-tyrosyl]-4-phenylpiperazine (informal name: KN-62 or KN62), which has the following structure:

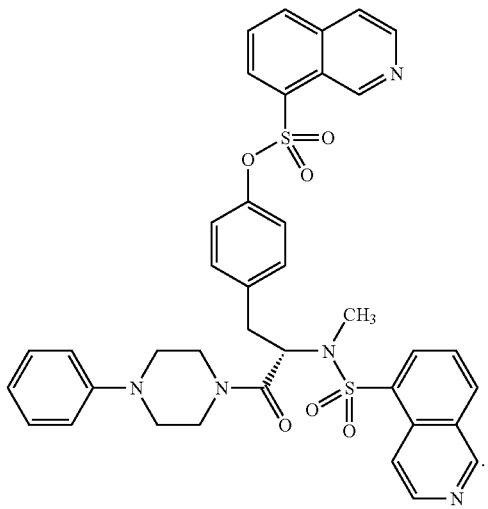

Example 2

ROCK Inhibitors Increase ES Cell Cloning Efficiency

Methods and Materials.

The experiments described in Example 1 were repeated with H-1152 (EMD Chemicals, Inc./Calbiochem; San Diego, Calif.) and Y-27632 (EMD Chemicals, Inc./Calbiochem). Briefly, H-1152 or Y-27632 was dissolved in DMSO to a concentration of 20 mM. H1 human ES cells were grown on Matrigel®—coated plates in TeSR™1 medium at a density of 100,000 cells per ml. H-1152 and Y-27632 were added to wells on their own plates at a final concentration of 20 μM, 15 μM, 10 μM or 5 μM in DMSO. DMSO and HA-100 (10 μM) were used as the negative and positive controls, respectively. The plates were treated every other day for a total of four days. Colony formation was detected with the ALP assay described above.

In a second experiment, H-1152 and Y-27632 were added to wells on their own plates at a final concentration of 5 μM, 500 nM, 50 nM or 5 nM in DMSO. DMSO and HA-100 (10 μM) were used as the negative and positive controls, respectively. The plates were treated as described above.

Results.

500 nM H-1152 and 5 μM Y-27632 showed the most colony formation with the ALP assay. The plates were examined by eye and were observed to be equal or better than HA-100 (at 10 μM) for concentrations above 500 nM for H-1152 and for concentrations above 5 μM for Y-27632.

The structure of H-1152 is as follows:

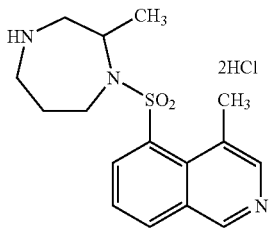

The structure of Y-27632 is as follows:

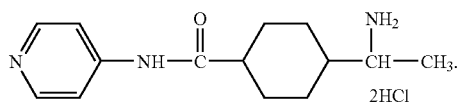

Although the foregoing invention has been described in some detail by way of illustration and example for purposes of clarity of understanding, it is understood that certain adaptations of the invention are a matter of routine optimization for those skilled in the art, and can be implemented without departing from the spirit of the invention, or the scope of the appended claims.

We claim:

1. A method of creating a clonal culture of human pluripotent stem cells comprising the steps of:
   providing a culture of human pluripotent stem cells in culture in a fibroblast growth factor-containing culture medium in a culture vessel;
   selecting a single pluripotent stem cell from the stem cells in culture;
   initiating a new culture of pluripotent stem cells with the single pluripotent stem cell in a culture vessel containing an extracellular matrix coating a surface inside the culture vessel and a fibroblast growth factor-containing culture medium, the culture medium including an agent selected to increase the cloning efficiency of the pluripotent stem cell culture relative to a pluripotent stem cell culture that does not contain the agent, the agent being a small molecule having the formula:

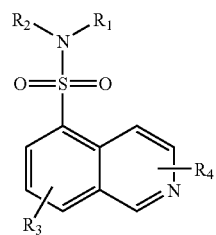

wherein $R_1$ and $R_2$ can form a cyclic group, or $R_1$ is H or an alkyl, and $R_2$ is H or an alkyl, and $R_1$ is not the same as $R_2$ unless $R_1$ and $R_2$ are part of a cyclic group; and wherein $R_3$ and $R_4$ are attached to any atom in the isoquinoline and are a hydrogen or an alkyl; and
   culturing the single pluripotent stem cell to create a clonal culture of human pluripotent stem cells.

2. The method as claimed in claim 1, wherein the agent is a kinase inhibitor.

3. The method as claimed in claim 1, wherein the agent is a protein kinase A inhibitor, a protein kinase C inhibitor, a protein kinase G inhibitor or a Rho-associated kinase (ROCK) inhibitor.

4. The method as claimed in claim 1, wherein the agent is selected from the group consisting of

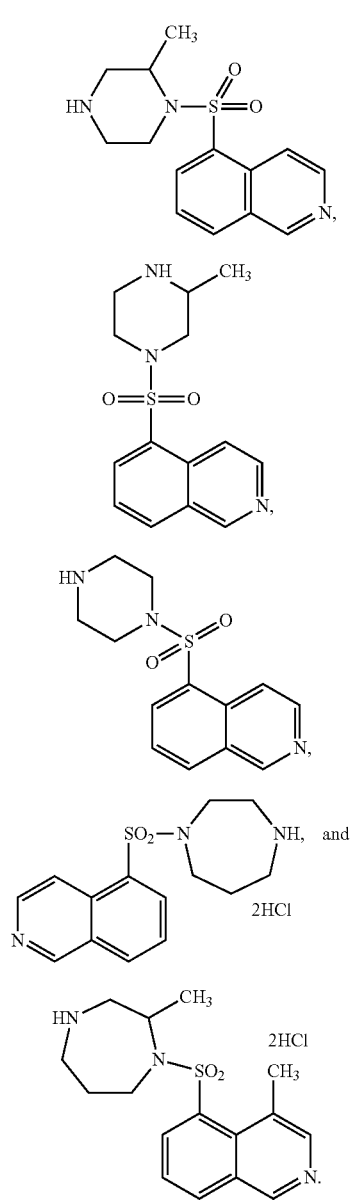
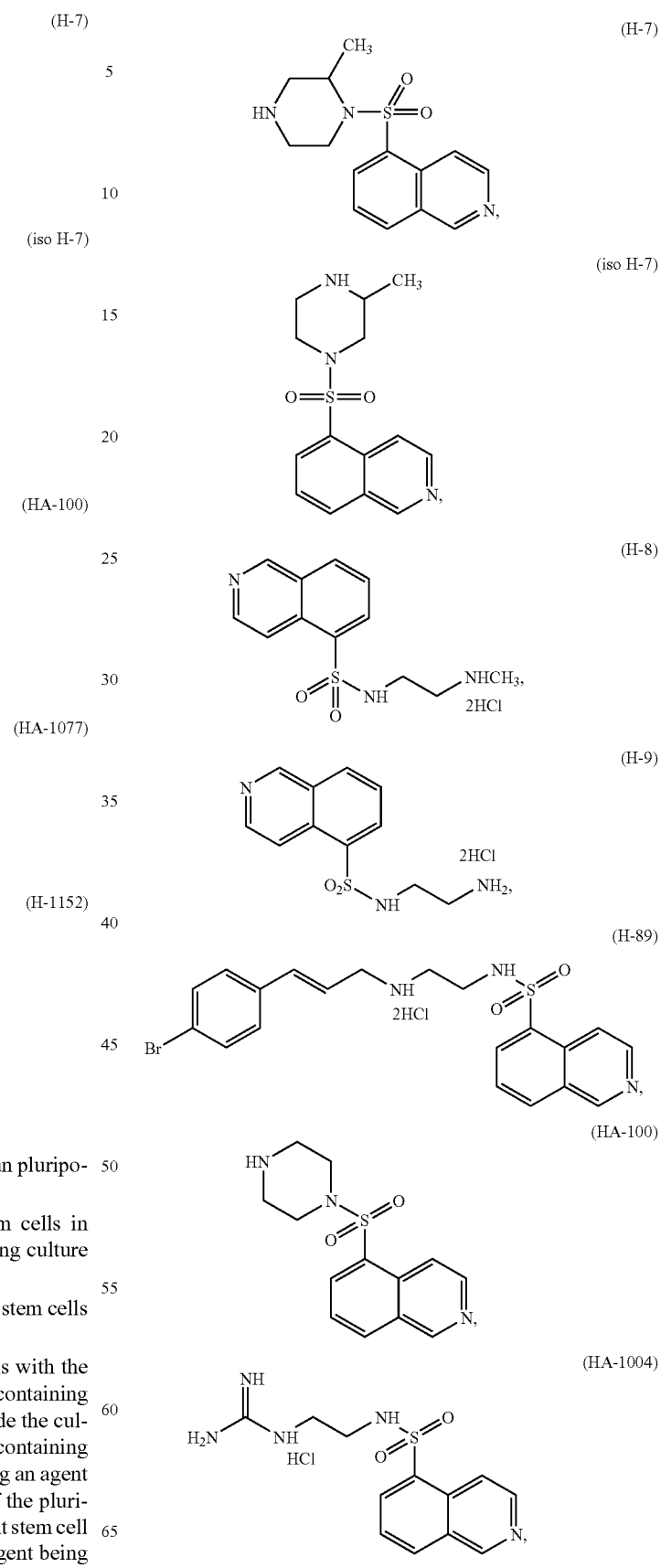

5. A method of creating a clonal culture of human pluripotent stem cells comprising the steps of;

providing a culture of human pluripotent stem cells in culture in a fibroblast growth factor-containing culture medium in a culture vessel;

selecting a single pluripotent stem cell from the stem cells in culture;

initiating a new culture of pluripotent stem cells with the single pluripotent stem cell in a culture vessel containing an extracellular matrix coating a surface inside the culture vessel and a fibroblast growth factor-containing culture medium, the culture medium including an agent selected to increase the cloning efficiency of the pluripotent stem cell culture relative to a pluripotent stem cell culture that does not contain the agent, the agent being selected from the group consisting of -continued

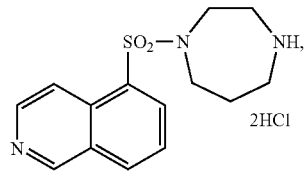
(HA-1077)

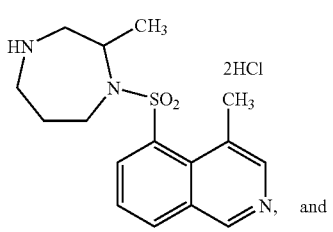
(H-1152)

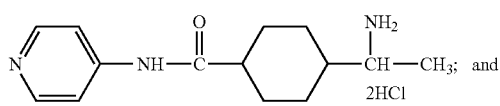
(Y-27632)

culturing the single pluripotent stem cell to create a clonal culture of human pluripotent stem cells.

6. A human pluripotent stem cell culture comprising:

a culture vessel containing an extracellular matrix coating a surface inside the culture vessel;

a fibroblast growth factor-containing culture medium;

human pluripotent stem cells growing in the fibroblast growth factor-containing culture medium; and the fibroblast growth factor-containing culture medium containing an agent selected to increase the cloning efficiency of the stem cell culture relative to a stem cell culture that does not contain the agent, the agent being a kinase inhibitor having the formula:

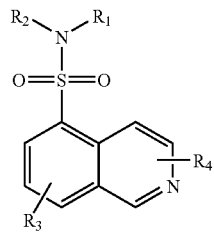

wherein $R_1$ and $R_2$ can form a cyclic group, or $R_1$ is H or an alkyl, and $R_2$ is H or an alkyl, and $R_1$ is not the same as $R_2$ unless $R_1$ and $R_2$ form a cyclic group; and wherein $R_3$ and $R_4$ are attached to any atom in the isoquinoline and are a hydrogen or an alkyl.

7. A human pluripotent stem cell culture of claim 6, wherein the agent is selected from the group consisting of

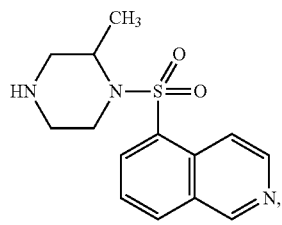
(H-7)

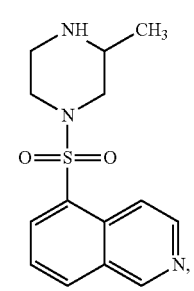
(iso H-7)

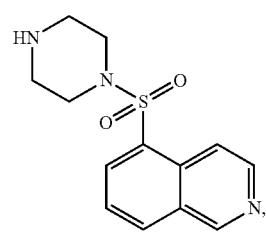
(HA-100)

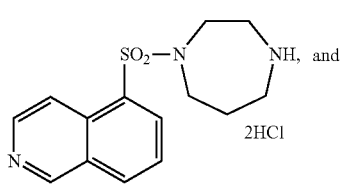
(HA-1077)

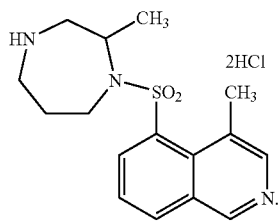
(H-1152)

8. An improvement in a fibroblast growth factor-containing medium in which to culture relative to a stem cell culture medium that does not contain the agent human pluripotent stem cells, the improvement comprising including in the medium an agent selected to increase the cloning efficiency of the stem cell culture, wherein the agent is selected from the group consisting of

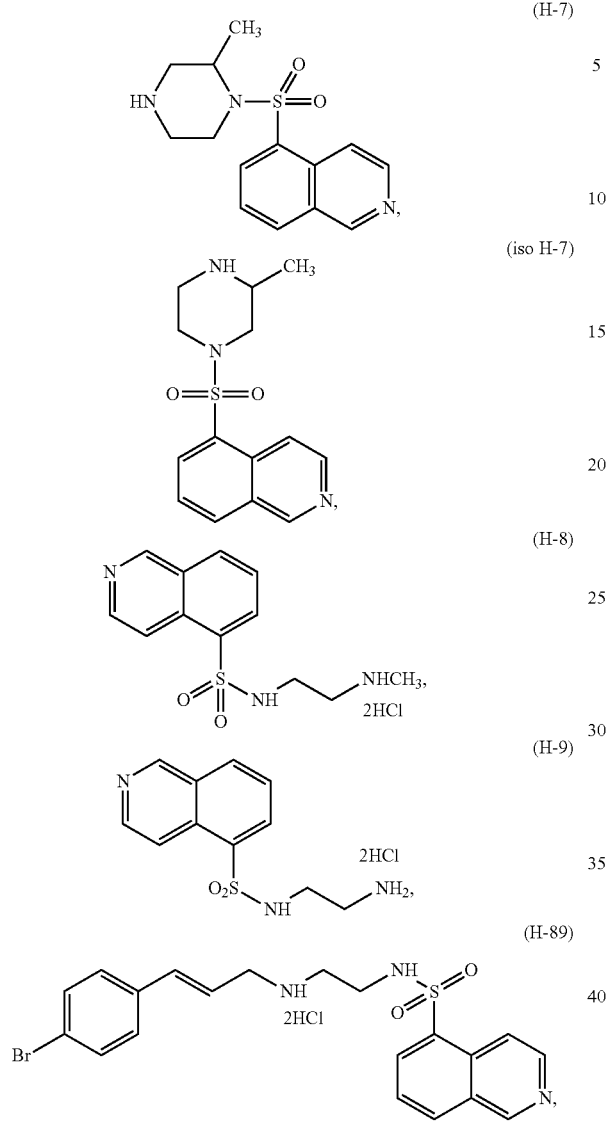
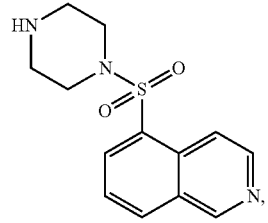
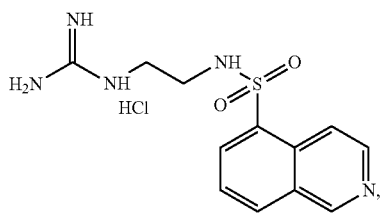
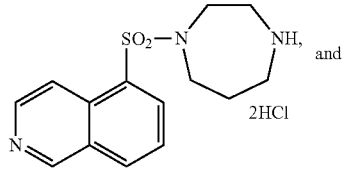
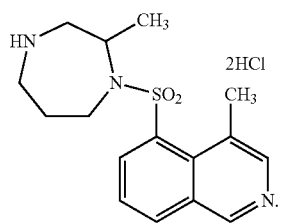
* * * * *